(12) United States Patent
Ahn et al.

(10) Patent No.: US 7,193,795 B2
(45) Date of Patent: Mar. 20, 2007

(54) OPTICAL SYSTEM WITH IMAGE PRODUCING SURFACE CONTROL UNIT

(75) Inventors: Hyeong-Min Ahn, Yongin-Si (KR); Dong-Hee Lee, Seongnam-Si (KR); Chang-Hyo Kim, Yongin-Si (KR); Hyoung-Jo Jeon, Suwon-Si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 328 days.

(21) Appl. No.: 10/790,791

(22) Filed: Mar. 3, 2004

(65) Prior Publication Data
US 2005/0094280 A1 May 5, 2005

(30) Foreign Application Priority Data
Nov. 4, 2003 (KR) .................. 10-2003-0077705

(51) Int. Cl.
*G02B 7/02* (2006.01)
(52) U.S. Cl. .................. 359/822; 396/342; 396/437
(58) Field of Classification Search ................ 359/822; 396/342, 437
See application file for complete search history.

(56) References Cited

U.S. PATENT DOCUMENTS

| 643,711 | A | * | 2/1900 | Carlton et al. | 396/437 |
| 2,974,574 | A | * | 3/1961 | Bohm et al. | 396/437 |
| 2003/0086143 | A1 | * | 5/2003 | Tsai | 359/210 |

FOREIGN PATENT DOCUMENTS

KR  10-2003-0052528  6/2003

* cited by examiner

*Primary Examiner*—Hung Xuan Dang
*Assistant Examiner*—Joseph Martinez
(74) *Attorney, Agent, or Firm*—Stanzione & Kim, LLP

(57) ABSTRACT

An optical system to attain a clear image of an object when the object is photographed in a state where an optical axis of a lens is inclined relative to the object, includes a lens which refracts light radiating from the object, an image producing surface on which the image of the object is produced according to the light refracted by the lens, and an image producing surface control unit which controls the image producing surface to move with respect to the lens. The image producing surface control unit includes an angle control unit to control an angle between an optical axis of the lens and the image producing surface.

27 Claims, 4 Drawing Sheets

OPTICAL SYSTEM WITH IMAGE PRODUCING SURFACE CONTROL UNIT

CROSS-REFERENCE TO RELATED APPLICATIONS

This application claims the benefit of Korean Patent Application No. 2003-77705, filed Nov. 4, 2003 in the Korean Intellectual Property Office, the disclosure of which is incorporated herein by reference.

BACKGROUND OF THE INVENTION

1. Field of the Invention

The present invention relates, in general, to an optical system to inspect defective parts of a flat panel display (FPD), such as a liquid crystal display (LCD) and, more particularly, to an optical system to attain a uniform and clear image of an object when the object inclined relative to an optical axis of a lens of the optical system is photographed.

2. Description of the Related Art

When defective parts on an FPD, such as an LCD, are inspected, an inspection result of the FPD may be varied according to viewing angles due to a characteristic of a viewing angular field of the FPD. Thus, when the FPD is photographed to inspect the defective parts thereof, it is necessary to photograph the FPD at a variety of angles as well as a vertical position with respect to the FPD.

To solve the above problem, there was proposed an optical system in Korean Patent Laid-Open Publication No. 2003-52528. According to the above Korean Patent Laid-Open Publication, an object was inspected using a common optical system and an inclined optical system. The common optical system photographs a surface of the object at a vertical position above the object. The inclined optical system photographs the surface of the object at an inclined position with respect to the object at a predetermined angle.

In the inclined optical system according to the above-mentioned Korean Patent Laid-Open publication, a CCD camera (charge-coupled device camera) which photographs a picture of the object must be placed to satisfy a specific equation. However, the conventional inclined optical system has a problem in that reference points of distances used in the specific equation are indefinite, thus the CCD camera may not be placed at a desired position. The conventional inclined optical system also has another problem in that it has no pickup unit to photograph the object at a variety of angles.

SUMMARY OF THE INVENTION

Accordingly, it is an aspect of the present invention to provide an inclined optical system capable of attaining a clear image of an object when an optical axis of a lens of the optical system is inclined relative to the object at a predetermined angle.

It is another aspect of the present invention to provide an optical system which is capable of clearly photographing an entire object at a variety of angles.

Additional aspects and/or advantages of the invention will be set forth in part in the description which follows and, in part, will be obvious from the description, or may be learned by practice of the invention.

The above and/or other aspects of the present invention are achieved by providing an optical system, which includes a lens to refract light radiating from an object, an image producing surface to produce an image according to the light refracted by the lens, and an image producing surface control unit to control the image producing surface with respect to the object and/or the lens.

According to another aspect of the invention, the image producing surface control unit may include an angle control unit to control an angle between an optical axis of the lens and the image producing surface. The angle control unit may include a distance adjusting unit provided at a position spaced apart from a rotative shaft of the optical system, and an elastic member mounted at a first end thereof to a base of the optical system and at a second end thereof a the body of the optical system.

According to yet another aspect of the invention, the lens is mounted to the lens, and the image producing surface is mounted to the body. The body may be coupled to the base by the rotative shaft to rotate relative to the base. A central axis of the rotative shaft and the image producing surface may be placed on the same plane. The image producing surface may rotate with respect to the central axis of the rotative shaft disposed on the same plane.

According to still another aspect of the invention, the body may include an outer frame supported by the rotative shaft, an inner frame mounted to the outer frame to rotate around a central axis of the outer frame, and a rear casing mounted to the inner frame and having the image producing surface mounted thereto. A charge-coupled device (CCD) may be provided at the image producing surface to convert the light radiating from the object into an electrical signal.

The above and/or other aspects of the present invention are achieved by providing an inclined optical system including a lens to refract light radiating from an object, and an image producing surface on which an image is produced using the light refracted by the lens. In this case, an optical axis of the lens is disposed at a predetermined angle with the object. When it is assumed that: the optical axis is expressed by X, an intersection point between a first main surface of the lens which faces the object and the optical axis X is expressed by a first main point $O_1$, and an intersection point between a second main surface of the lens which faces the image producing surface and the optical axis X is expressed by a second main point $O_2$; a first point on the object is expressed by A, a foot of the first point A in a direction perpendicular to the optical axis X is expressed by $A_0$, a distance between the foot $A_0$ and the first main point $O_1$ is expressed by $s_2$, an image of the first point A produced on the image producing surface is expressed by A', a foot of a perpendicular from the image A' to the optical axis X is expressed by $A'_0$, and a distance between the foot $A'_0$ and the second main point $O_2$ is expressed by $s'_2$; and a second point on the object is expressed by C, a foot of a perpendicular from the second point C to the optical axis X is expressed by $C_0$, a distance between the foot $C_0$ and the first main point $O_1$ is expressed by $s_3$, an image of the second point C produced on the image producing surface is expressed by C', a foot of in a direction the image C' perpendicular to the optical axis X is expressed by $C'_0$, and a distance between the foot $C'_0$ and the second main point $O_2$ is expressed by $s'_3$, the image producing surface is inclined relative to the optical axis X of the lens so that the distance $s'_2$ is shorter than the distance $s'_3$ when the distance $s_2$ is longer than the distance $s_3$.

According to another aspect of the invention, in the inclined optical system, when the first point A is set so that a distance between the foot $A_0$ and the first main point $O_1$ is farthest, and the second point C is set so that a distance between the foot $C_0$ and the first main point $O_1$ is nearest.

When it is assumed that: a focal distance of the lens is expressed by f, an intersection point between the object and the optical axis X of the lens is expressed by B, a distance between the intersection point B and the first main point $O_1$ is expressed by $s_1$, an image of the intersection point B produced on the image producing surface is expressed by B', and a distance between the image B' and the second main point $O_2$ is expressed by $s'_1$, the image producing surface is inclined relative to the optical axis X of the lens to satisfy the following Equation $1/s_1+1/s'_1=1/f$ and to satisfy at least one of the following Equations $1/s_2+1/s'_2=1/f$ and $1/s_3+1/s'_3=1/f$.

According to yet another aspect of the invention, in the inclined optical system, when it is assumed that: an intersection point between the first main surface and a line extending through the first point A and the second point C is expressed by D, and an intersection point between the second main surface and a line extending through the image A' and the image C' is expressed by E, the image producing surface is inclined relative to the optical axis X of the lens so that a line extending through the intersection point D and the intersection point E is parallel to the optical axis X.

The above and/or other aspects of the present invention are achieved by providing an inclined optical system, which includes a lens to refract light radiating from an object, and an image producing surface on which an image is produced using the light refracted by the lens, the lens and the image producing surface inclined in opposite directions relative to an optical axis of the lens.

BRIEF DESCRIPTION OF THE DRAWINGS

These and/or other aspects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Figure 1:
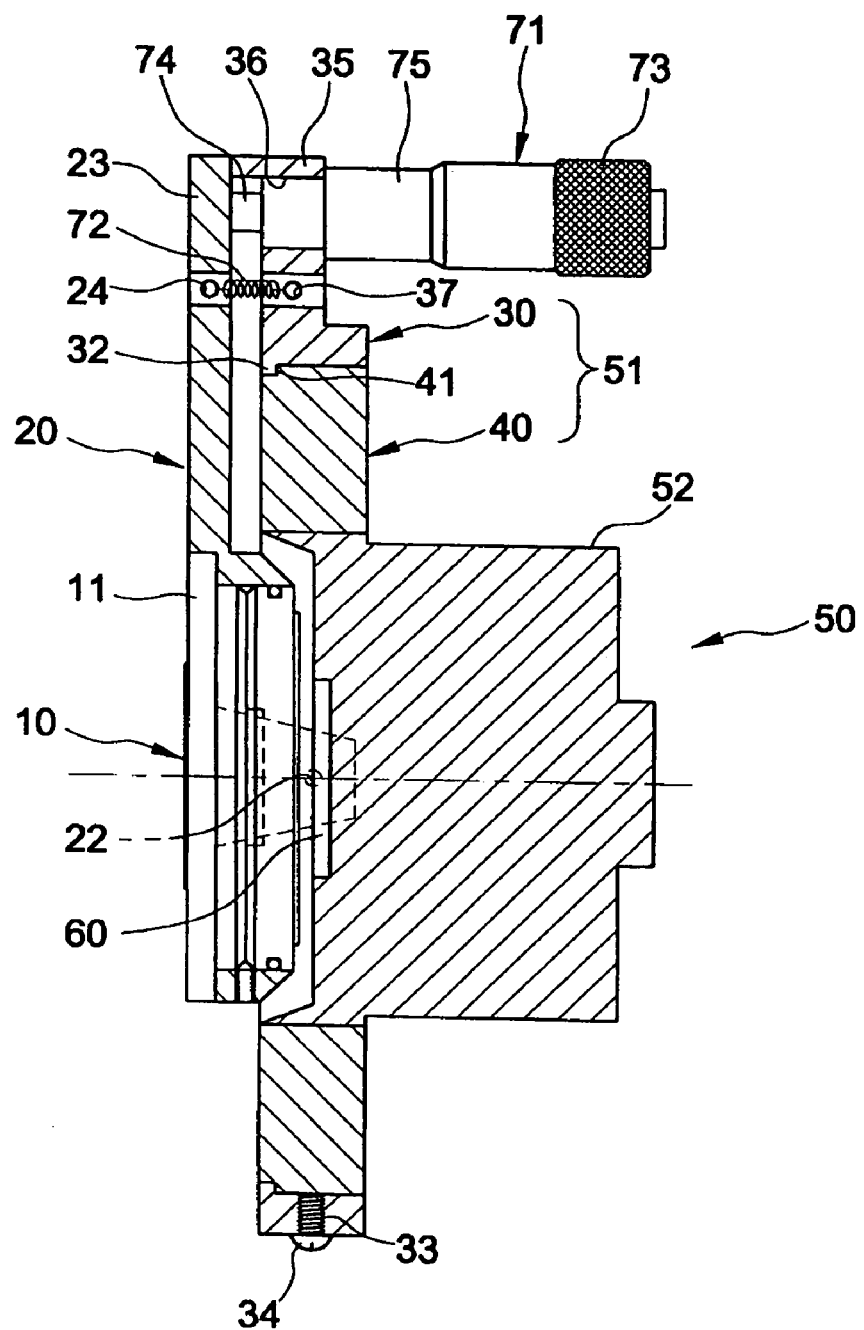
FIG. 1 is a sectional view of an optical system having an image producing surface control unit according to an embodiment of the present invention.

Reference will now be made in detail to the preferred embodiment of the present invention, examples of which are illustrated in the accompanying drawings, wherein like reference numerals refer to like elements throughout. The embodiment is described below in order to explain the present invention by referring to the figures.

Figure 2:
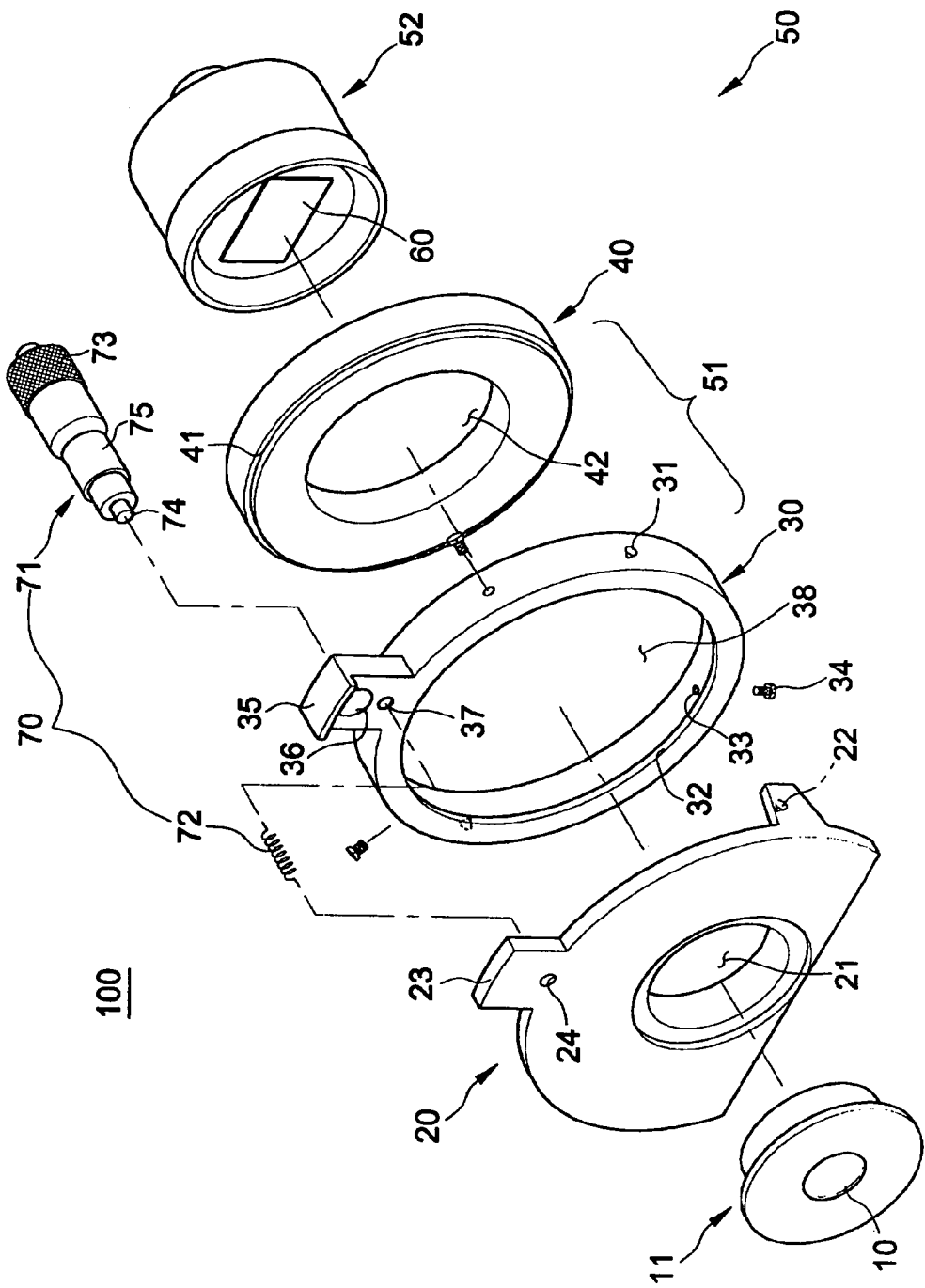
FIG. 2 is an exploded perspective view of the optical system of FIG. 1.

FIG. 1 is a sectional view of an optical system 100 having an image producing surface control unit according to an embodiment of the present invention. FIG. 2 is an exploded perspective view of the optical system 100 of FIG. 1.

As shown in FIGS. 1 and 2, the optical system 100 includes a lens 10, a lens holder 11, a base 20, a body 50, and an angle control unit 70. The lens 10 refracts light radiating from an object T to be inspected, and is mounted to the lens holder 11. To the base 20 is mounted the lens holder 11. The body 50 is rotatably mounted to the base 20. The angle control unit 70 is provided on upper portions of both the base 20 and the body 50.

The body 50 includes a frame 51, a rear casing 52, and an image producing surface 60. The frame 51 is coupled to the base 20 by tilting shafts 22 to tilt relative to the base 20. The rear casing 52 is mounted to the frame 51. The image producing surface 60 is provided on a predetermined portion of the rear casing 52 to produce an image (signal) according to the light refracted by the lens 10. The frame 51 includes an outer frame part 30 which is coupled to the base 20 by the tilting shafts 22, and an inner frame part 40 which is seated (disposed) in the outer frame part 30 to rotate around a central axis of the outer frame part 30. The rear casing 52 may be fixedly mounted to the inner frame part 40.

The lens 10 is held by the holder 11 to be disposed on a central portion of the lens holder 11. The lens holder 11 is seated (disposed) in a circular seating opening 21 provided on a central portion of the base 20. The outer frame part 30 is coupled to the base 20 by the tilting shafts 22 provided on both side ends of the base 20. To couple the outer frame part 30 to the base 20, shaft mounting holes 31 are provided on an outer surface of the outer frame part 30 at positions corresponding to the tilting shafts 22 of the base 20. On a central portion of the outer frame part 30 is provided a first seat opening 38 so that the inner frame part 40 is seated (disposed) in the seat opening 38 of the outer frame part 30. Further, a stepped portion 41 is provided along an outer edge of a front surface of the inner frame part 40, and a locking step 32 is inwardly projected from an edge of the outer frame part 30 corresponding to the first seat opening 38 so that the stepped portion 41 of the inner frame part 40 is seated (disposed) on the locking step 32 of the outer frame part 30. A plurality of screw holes 33 are provided along the outer surface of the outer frame part 30. The inner frame part 40 is fastened to the outer frame part 30 by tightening a plurality of screws 34 into the outer frame part 30 through the screw holes 33.

The image producing surface 60 is provided on a central portion of a front portion of the rear casing 52 to produce an image according to the light passing through the lens 10 and impinging on the image producing surface 60. A charge-coupled device (CCD) is provided on a predetermined portion of the image producing surface 60 to convert the light into an electrical signal corresponding to the image of the object T. The electrical signal output from the CCD is transmitted to an image processing unit (not shown) to process the electrical signal. The rear casing 52 is seated (disposed) in a second seat opening 42 provided on a central portion of the inner frame part 40. Further, after the inner frame part 40 is seated in the first seat opening 38 of the outer frame part 30, the inner frame part 40 is fastened to the outer frame part 30 by tightening the screws 34 into the outer frame part 30 through the screw holes 33. In this case, because the inner frame part 40 is fastened to the outer frame part 30 by the screws 34, the inner frame part 40 may be loosened from the outer frame part 30 by manipulating the screws 34 when necessary. Thus, when the image producing surface 60 is required to rotate on a same plane, that is, when the image producing surface 60 is required to rotate with respect to its central axis (or optical axis) without tilting the image producing surface, the screws 34 are loosened from the screw holes 33 to allow the inner frame part 40 to rotate relative to the outer frame part 30. At this time, the rear casing 52 rotates along with the inner frame part 40, thus allowing the image producing surface 60 to rotate with respect to the same plane as the tilting shafts 22 to a desired angle.

The angle control unit 70 functions to control a tilting angle of the image producing surface 60 with respect to the base 20 of the lens 10. The angle control unit 70 includes a distance adjusting unit 71 and an elastic member 72. The distance adjusting unit 71 is provided at a predetermined portion of the outer frame part 30 to adjust a distance between the outer frame part 30 and the base 20, thereby adjusting the tilting angle of the image producing surface 60. The elastic member 72 is mounted at a first end thereof to the base 20 and at a second end thereof to the outer frame part 30. The distance adjusting unit 71 includes a thimble 73, a spindle 74, and a sleeve 75. The thimble 73 is a part of a micrometer to measure a distance and rotates around a central axis thereof. The spindle 74 advances or retracts along the central axis of the thimble 73 according to a rotating direction of the thimble 73. The sleeve 75 supports both the thimble 73 and the spindle 74. The elastic member 72 may be a tension spring to bias the base 20 in a direction toward the outer frame part 30.

To mount the distance adjusting unit 71 and the elastic member 72 to the outer frame part 30, a support bracket 23 upwardly projects from an upper end of the base 20, and a first support hole 24 is provided on a predetermined portion of the support bracket 23 to support the first end of the elastic member 72. Further, a mount bracket 35 upwardly projects from an upper end of the outer frame part 30, and a mount hole 36 is provided on a predetermined portion of the mount bracket 35 to mount the sleeve 75 of the distance adjusting unit 71 to the outer frame part 30. A second support hole 37 is provided on a predetermined portion of the mount bracket 35 around the mount hole 36 to support the second end of the elastic member 72. The mount bracket 35 and the sleeve 75 are coupled to each other using threaded portions formed thereon when a portion of the distance control unit 71 is inserted into the mount hole 36. The spindle 14 protrudes and is retreated with respect to the sleeve 75 so that the image producing surface 60 moves with respect to the base 20 and/or the lens 10 according to a rotation of the thimble 73 and/or a movement of the spindle 74.

In this case, the lens holder 11, the base 20, the outer framer part 30, the inner frame part 40, and the rear casing 52 are placed along an optical axis X of the lens 10, i.e., a central axis of the above-mentioned elements. In the present invention, a central axis of the tilting shafts 22 of the outer frame part 30 and the base 20 is preferably placed on the same plane as the image producing surface 60.

The present invention further provides an inclined optical system using the above-mentioned optical system 100. The inclined optical system of the present invention will be described in the following.

Figure 3:
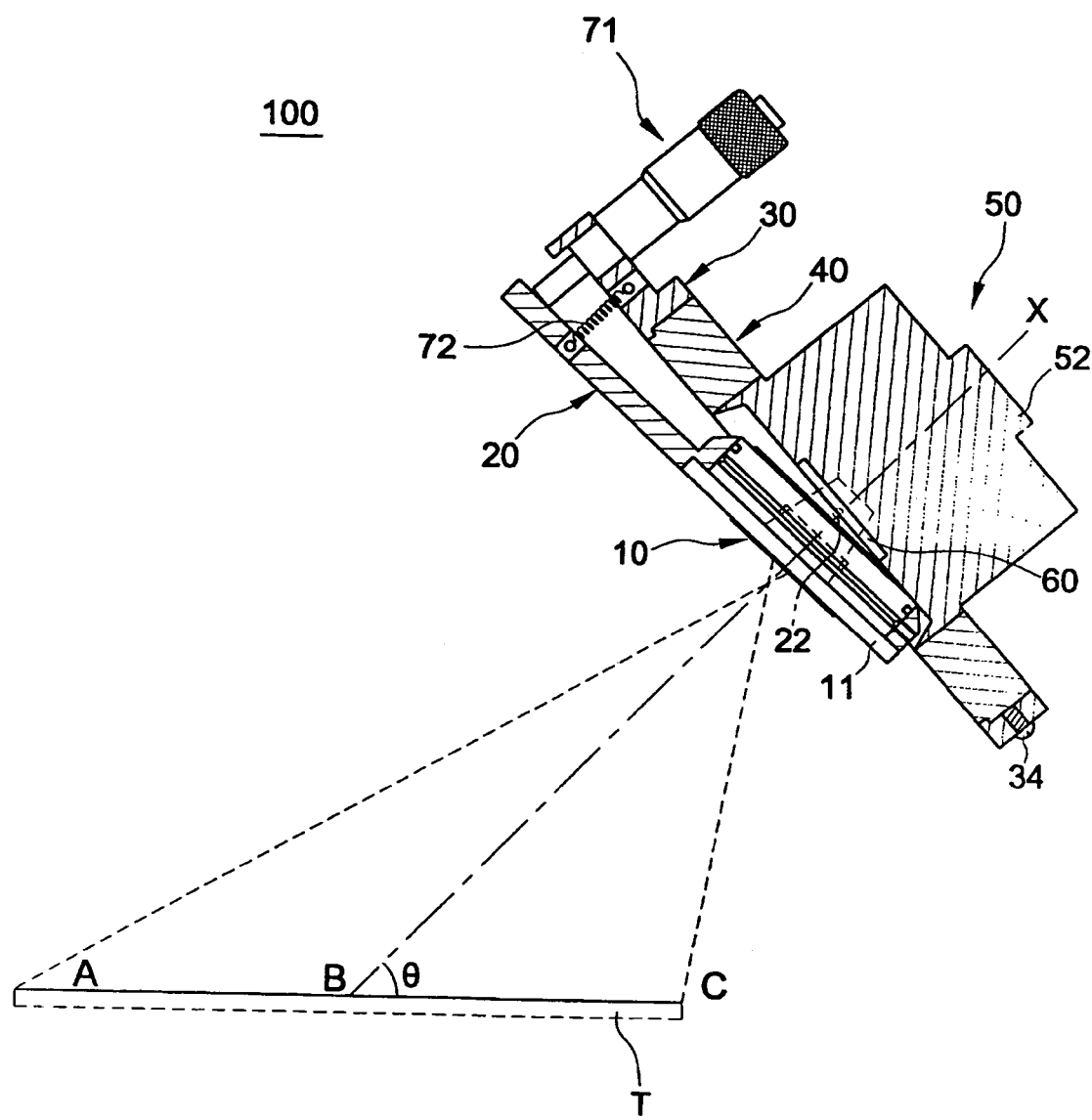
FIG. 3 is a sectional view to show a state where a surface of an object which is inclined relative to an optical axis of a lens of the optical system is photographed by the optical system of FIG. 1.

As shown in FIG. 3, when the inclined optical system photographs a surface of the object T inclined so that the optical axis X of the lens 10 is at an angle of θ with the surface of the object T, an angle between the image producing surface 60 and the optical axis X is controlled to satisfy the following relations, thus attaining a clear image of the object T.

Figure 4:
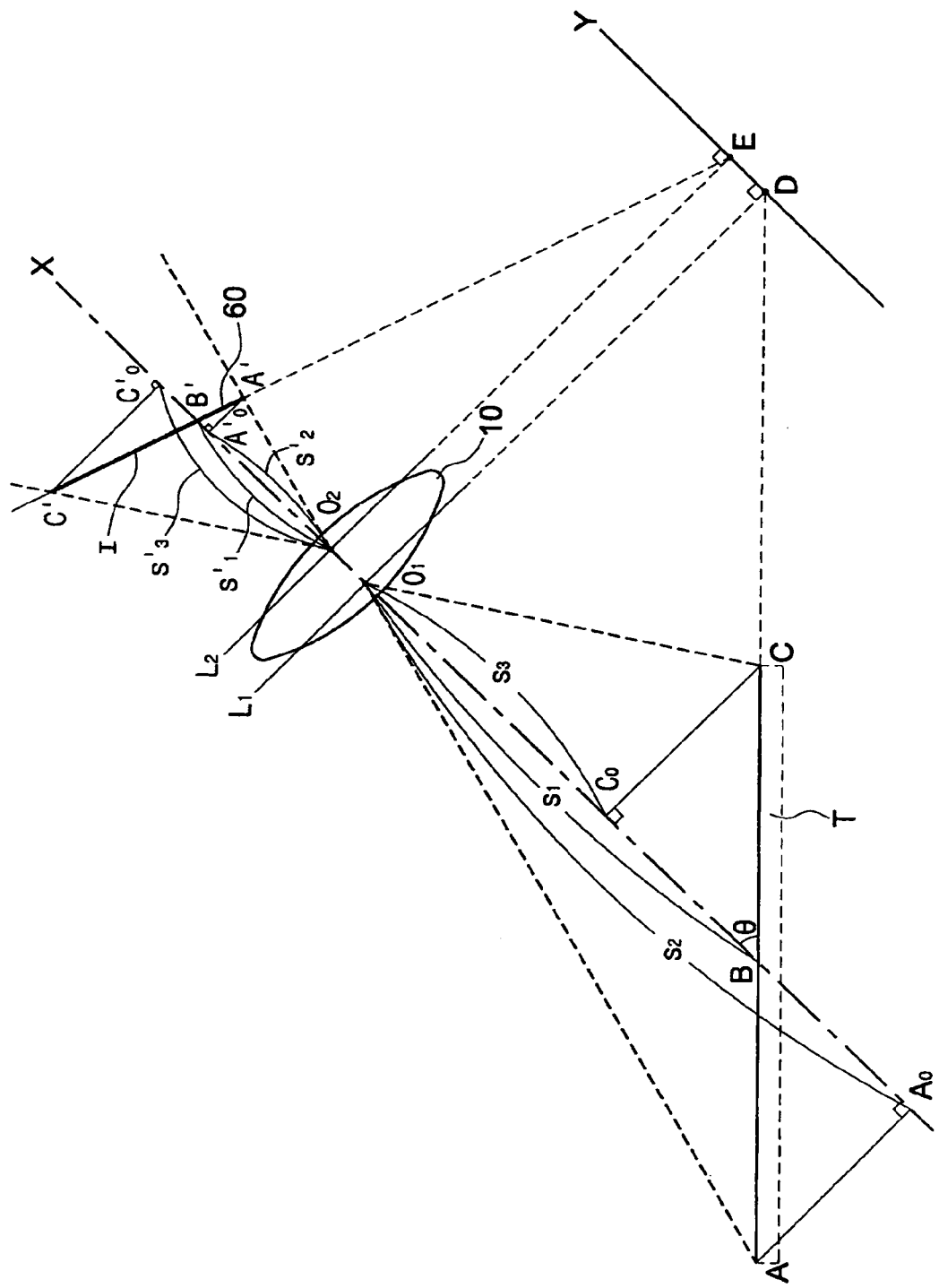
FIG. 4 is a view to show a photographing principle of the optical system of FIG. 3.

As shown in FIG. 4, when it is assumed that: an intersection point between a first main surface $L_1$ of the lens 10, which faces the object T, and the optical axis X is expressed by a first main point $O_1$, and an intersection point between a second main surface $L_2$ of the lens 10, which faces the image producing surface 60, and the optical axis X is expressed by a second main point $O_2$; an intersection point between the optical axis X and the object T is expressed by B, a first point set on the object T so that a distance between the first main point $O_1$ and a foot of the first point is the farthest, is expressed by A, a second point set on the object T so that a distance between the first main point $O_1$ and a perpendicular foot of the second point is the nearest, is expressed by C, the perpendicular foot of the point A to the optical axis X is expressed by $A_0$, the perpendicular foot of the point C to the optical axis X is expressed by $C_0$, a distance between the first main point $O_1$ and the foot $A_0$ is expressed by $s_2$, a distance between the first main point $O_1$ and the intersection point B is expressed by $s_1$, and a distance between the first main point $O_1$ and the foot $C_0$ is expressed by $s_3$; and in an image I of the object T produced on the image producing surface 60, an image of the point A is expressed by A', an image of the intersection point B is expressed by B', an image of the point C is expressed by C', a foot of a perpendicular from the image A' to the optical axis X is expressed by $A'_0$, a perpendicular foot of the image C' to the optical axis X is expressed by $C'_0$, a distance between the second main point $O_2$ and the foot $A'_0$ is expressed by $s'_2$, a distance between the second main point $O_2$ and the image B' is expressed by $s'_1$, and a distance between the second main point $O_2$ and the foot $C'_0$ is expressed by $s'_3$, in the lens 10 having a focal distance f, the distance $s'_1$ is determined according to a position relation among the lens 10, the tilting shafts 22, and the image producing surface 60 of the optical system according to the present invention. Further, the optical system of the present invention is arranged according to the distance $s_1$ between the lens 10 and the object T which is controlled to satisfy the following Equation [1].

$$1/s_1 + 1/s'_1 = 1/f \qquad [1]$$

Furthermore, the distance adjusting unit 71 is controlled to satisfy either one of the following Equations [2] and [3], thereby controlling an angle between the image producing surface 60 and the optical axis X and obtaining a clear image of the object T.

$$1/s_2 + 1/s'_2 = 1/f \qquad [2]$$

$$1/s_3 + 1/s'_3 = 1/f \qquad [3]$$

According to an aspect of the invention, when the distance $s_1$ between the object T and the lens 10 and the angle between the image producing surface 60 and the optical axis X are controlled to satisfy all of the above-mentioned Equations [1] to [3], a most clear image of the object T is obtained. In this case, assuming that an intersection point between a line AC and the first main surface $L_1$ is expressed by D, and an intersection point between a line A'C' and the second main surface $L_2$ is expressed by E, a line Y extending through the intersections D and E is disposed parallel to the optical axis X.

Further, in the Equation [2], the focal distance of the lens 10 is constant. Thus, as the distance $s_2$ is increased, the distance $s'_2$ is reduced. To obtain the desired clear image, when the distance $s_1$ between the object T and the first main point $O_1$ is increased, the distance $s'_1$ between the second main point $O_2$ and the image producing surface 60, on which the image of the object T is produced, must be reduced. In a detailed description, the object T and the image producing surface 60 must be inclined in opposite directions relative to the optical axis X.

As is apparent from the above description, the present invention provides an optical system in which an angle control unit is controlled according to an angle between an object to be photographed and an optical axis of a lens, thus attaining a clear image of the object. Further, when the object is photographed several times while variously changing the angle between the object and the optical axis of the lens, the angle control unit is controlled according to the angles between the object and the optical axis of the lens, thus attaining clear images of the object. Moreover, the optical system can detect any defected parts disposed on a first portion of the object T between A and B as well as a second portion of the object T between B and C.

Although an embodiment of the present invention has been shown and described, it would be appreciated by those skilled in the art that changes may be made in these embodiments without departing from the principles and spirit of the invention, the scope of which is defined in the claims and their equivalents.

What is claimed is:

1. An optical system, comprising:
   a lens to refract light radiating from an object;
   an image producing surface on which an image corresponding to the object is produced according to the light refracted by the lens; and
   an image producing surface control unit to control the image producing surface to move with respect to the lens, the image producing surface control unit comprising an angle control unit located at a position spaced apart from an optical axis of the lens to control an angle between the optical axis of the lens and the image producing surface.

2. The optical system according to claim 1, further comprising:
   a base to which the lens is mounted, and having a rotative shaft; and
   a body to which the image producing surface is mounted, the body coupled to the base by the rotative shaft to rotate relative to the base.

3. The optical system according to claim 2, wherein a central axis of the rotative shaft and the image producing surface are placed on the same plane.

4. The optical system according to claim 2, wherein the image producing surface rotates with respect to the same plane as the rotative shaft.

5. The optical system according to claim 4, wherein the body comprises:
   an outer frame supported by the rotative shaft;
   an inner frame mounted to the outer frame to rotate around a central axis of the outer frame; and
   a rear casing mounted to the inner frame, the image producing surface mounted to the rear casing.

6. The optical system according to claim 5, further comprising:
   a charge-coupled device (CCD) provided on the image producing surface to convert the light radiating from the object into an electrical signal corresponding to at least one portion of the object.

7. The optical system according to claim 2, wherein the angle control unit comprises:
   a distance adjusting unit provided at a position which is spaced apart from the rotative shaft.

8. The optical system according to claim 7, wherein the angle control unit further comprises:
   an elastic member having a first end mounted to the base, and a second end mounted to the body.

9. The optical system according to claim 7, wherein the distance adjusting unit comprises:
   a thimble to rotate around a central axis thereof;
   a spindle to advance or retract according to a rotating direction of the thimble; and
   a sleeve to support both the thimble and the spindle.

10. An inclined optical system, comprising:
    a lens to refract light radiating from an object; and
    an image producing surface on which an image is produced by the light refracted by the lens,
    wherein an optical axis of the lens is disposed at a predetermined angle with the object, and wherein, when the optical axis is expressed by X, an intersection point between a first main surface of the lens, which faces the object, and the optical axis X is expressed by a first main point $O_1$, and an intersection point between a second main surface of the lens, which faces the image producing surface, and the optical axis X is expressed by a second main point $O_2$, when a first point on the object is expressed by A, a foot of the first point A perpendicular to the optical axis X is expressed by $A_0$, a distance between the foot $A_0$ and the first main point $O_1$ is expressed by $s_2$, an image of the first point A produced on the image producing surface is expressed by A', a foot of the image A' perpendicular to the optical axis X is expressed by $A'_0$, and a distance between the foot $A'_0$ and the second main point $O_2$ is expressed by $s'_2$, and when a second point on the object is expressed by $C_0$, a foot of the second point C perpendicular to the optical axis X is expressed by $C_0$, a distance between the foot $C_0$ and the first main point $O_1$ is expressed by $s_3$, an image of the second point C produced on the image producing surface is expressed by C', a foot of the image C' perpendicular to the optical axis X is expressed by $C'_0$, and a distance between the foot $C'_0$ and the second main point $O_2$ is expressed by $s'_3$, the image producing surface is inclined relative to the optical axis X of the lens so that the distance $s'_2$ is shorter than the distance $s'_3$ when the distance $s_2$ is longer than the distance $s_3$.

11. The inclined optical system according to claim 10, wherein, when the first point A is set so that the distance $s_2$ between the foot $A_0$ and the first main point $O_1$ is a predetermined distance, and when a focal distance of the lens is expressed by f, an intersection point between the object and the optical axis X of the lens is expressed by B, a distance between the intersection point B and the first main point $O_1$ is expressed by $s_1$, an image of the intersection point B produced on the image producing surface is expressed by B', and a distance between the image B' and the second main point $O_2$ is expressed by $s'_1$, the image producing surface is inclined relative to the optical axis X of the lens to satisfy both the following Equations:

$$1/s_1+1/s'_1=1/f \text{ and } 1/s_2+1/s'_2=1/f.$$

12. The inclined optical system according to claim 11, wherein, when the second point C is set so that the distance $s_3$ between the foot $C_0$ and the first main point $O_1$ is another predetermined distance, the image producing surface is inclined relative to the optical axis X of the lens to satisfy the following Equation:

$$1/s_3+1/s'_3=1/f.$$

13. The inclined optical system according to claim 10, wherein, when the second point C is set so that the distance $s_3$ between the foot $C_0$ and the first main point $O_1$ is a predetermined distance, and when a focal distance of the lens is expressed by f, an intersection point between the object and the optical axis X of the lens is expressed by B, a distance between the intersection point B and the first main point $O_1$ is expressed by $s_1$, an image of the intersection point B produced on the image producing surface is expressed by B', and a distance between the image B' and the second main point $O_2$ is expressed by $s'_1$, the image producing surface is inclined relative to the optical axis X of the lens to satisfy both the following Equations:

$$1/s_1 + 1/s'_1 = 1/f \text{ and } 1/s_3 + 1/s'_3 = 1/f.$$

14. The inclined optical system according to claim 10, wherein, when an intersection point between the first main surface and a line extending through the first point A and the second point C is expressed by D, and an intersection point between the second main surface and a line extending through the image A' and the image C' is expressed by E, the image producing surface is inclined relative to the optical axis X of the lens so that a line extending through the intersection point D and the intersection point E is parallel to the optical axis X.

15. An optical system, comprising:
a lens to refract light radiating from an object;
an image producing surface on which an image is produced according to the light refracted by the lens, the lens and the image producing surface inclined in opposite directions relative to an optical axis of the lens;
a base on which the lens is mounted;
a body on which the image producing surface is mounted;
an angle control unit mounted to the body to push the base with respect to the body to control an angle between the optical axis of the lens and the image producing surface; and
an elastic member to bias the body towards the base.

16. The optical system according to claim 15, wherein the image producing surface is movably disposed to be inclined with respect to a line perpendicular to the optical axis of the lens.

17. The optical system according to claim 15, wherein the lens is disposed on a first plane perpendicular to the optical axis of the lens, and the image producing surface is inclined with respect to the first plane of the lens.

18. The optical system according to claim 17, wherein the object is disposed on a second plane inclined with respect to the optical axis of the lens.

19. The optical system according to claim 15, wherein the object comprises first and second portions disposed opposite to each other with respect to the optical axis of the lens, and the image producing surface moves with respect to the lens so that the image corresponding to the first and second portions of the object is clearly obtained on the image producing surface.

20. The optical system according to claim 15, wherein the object comprises a first and second portions, the image comprises a first sub-image and a second sub-image corresponding to first and second portions of the object, respectively, and the image producing surface is inclined relative to the optical axis of the lens so that a distance from the lens to the first sub-image is shorter than a distance from the lens to the second sub-image when a distance from the lens to the first portion of the object is longer than a distance from the lens to the second portion of the object.

21. The optical system according to claim 20, wherein the image producing surface is inclined relative to the optical axis of the lens to satisfy that an inverse number of a focal distance of the lens is equal to both a first sum of an inverse number of a distance from the lens to an intersection between the optical axis and the object and an inverse number of a distance from the lens to an intersection between the optical axis and the image, and a second sum of an inverse number of the distance from the lens to the first portion of the object and an inverse number of the distance from the lens to the first sub-image.

22. The optical system according to claim 21, wherein the inverse number of the focal distance of the lens is equal to a sum of an inverse number of the distance from the lens to the second portion of the object and an inverse number of the distance from the lens to the second sub-image.

23. The optical system according to claim 20, wherein the first portion of the object is disposed opposite to the first sub-image with respect to the optical axis of the lens, and the second portion of the object is disposed opposite to the second sub-image with respect to the optical axis of the lens.

24. The optical system according to claim 15, further comprising:
a base on which the lens is mounted;
at least one shaft formed on the base;
a frame on which the image producing surface is mounted, the frame having at least one shift mounting hole to receive the at least one shaft; and
an image producing surface control unit to move the frame with respect to the base.

25. The optical system according to claim 24, wherein the base comprises a portion extending toward the frame in a direction parallel to the optical axis of the lens, and the at least one shaft is formed on the portion of the base in a direction substantially perpendicular to the optical axis of the lens to be inserted into the at least one shaft mounting hole.

26. The optical system according to claim 25, wherein the image producing surface control unit comprises a distance adjusting unit disposed on a portion of the frame other than the at least one shaft mounting hole, and the distance adjusting unit comprises a spindle advancing and retracting with respect to the frame to move the frame toward and away from the base with respect to the at least one shaft.

27. An optical system, comprising:
a base having a lens to refract light radiating from an object;
a body having an image producing surface on which an image of the object is produced according to the light refracted by the lens; and
an angle control unit disposed on a first end of the body to control an angle between the lens and the image producing surface with respect to a second end of the body disposed opposite to the first end with respect to the image producing surface.

* * * * *